(12) United States Patent
Kobayashi et al.

(10) Patent No.: US 6,576,711 B2
(45) Date of Patent: Jun. 10, 2003

(54) RESIN MATERIAL FOR DENTURE BASE

(75) Inventors: Kenichi Kobayashi, Tokyo (JP); Tomohiro Kumagai, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/948,775

(22) Filed: Sep. 10, 2001

(65) Prior Publication Data
US 2002/0061937 A1 May 23, 2002

(30) Foreign Application Priority Data
Sep. 19, 2000 (JP) ......................................... 2000-283941

(51) Int. Cl.$^7$ .............................. A61F 2/00; C08J 3/00; C08K 3/20; C08L 33/00; C08F 265/04

(52) U.S. Cl. ........................ 525/309; 523/115; 523/120

(58) Field of Search ................................ 523/115, 120; 525/309

(56) References Cited
FOREIGN PATENT DOCUMENTS
GB 2347679 A * 9/2000

* cited by examiner

*Primary Examiner*—Patrick D. Niland
(74) *Attorney, Agent, or Firm*—Oblon, Spivak, McClelland, Maier & Neustadt, P.C.

(57) ABSTRACT

A resin material for denture base that is less in possibility to incorporate air bubbles into a mixed material, exhibits a proper elasticity during the elimination from an oral cavity, not causing deformation, and can impress precisely the state in the oral cavity, is provided. The resin material for denture base is of a two-liquid type, constructed by (a) a methacrylate or acrylate monomer having at least one unsaturated double bond; (b) one or two or more polymers selected from the group consisting of a methacrylate polymer, an acrylate polymer, a methacrylate/acrylate copolymer, a methacrylate/styrene copolymer, and an acrylate/styrene copolymer; and (c) a polymerization initiator, wherein a liquid A comprises the polymer (b), the monomer (a) having a solubility to the polymer (b) of 20% by weight or more, and the polymerization initiator (c); and a liquid B comprises the polymer (b) and the monomer (a) having a solubility to the polymer (b) of less than 20% by weight.

18 Claims, No Drawings

RESIN MATERIAL FOR DENTURE BASE

BACKGROUND OF THE INVENTION

1. Field of the Invention

The present invention relates to a resin material for denture base that is used mainly for relining (rebasing) of a denture base. Particularly, the invention relates to a two-liquid mixing type resin material for denture base, which is superior in operability and can be used by a simple operation of only mixing two liquids with each other during the use.

2. Description of the Conventional Art

Hitherto, the relining (or rebasing) of a denture base has been carried out in an indirect method. That is, a denture base in which one layer of a mucosal surface has been deleted is used as a tray; an impression material is built up thereon, thereby taking a functional impression; the resulting denture base is invested in a flask using an investment as it stands; the impression material is then eliminated, thereby forming a space in the investment; thereafter, according to the same procedures as in the preparation of a denture base, necessary amounts of a liquid and a powder for a resin material for denture base are weighed, and mixed and mixed by means of a spatula or the like; the mixed material in a dough-like state is filled in the space in the investment within the flask; the dough is heated for polymerization and curing as it stands; and after cooling the cured material is separated from the investment, followed by forming the surface characterization and polishing.

However, since it takes a long period of time to carry out the relining by this indirect method, a direct method using a low temperature polymerization type or photopolymerization type resin material for denture base is being frequently employed. The direct method is carried out in the following manner. That is, after deleting one layer in a mucosal surface side of a denture base, necessary amounts of a liquid and a powder for a resin material for denture base are weighed, and mixed with each other; the mixed material in a dough-like state is built up directly in the mucosal surface side of the denture base; the resulting material is inserted into an oral cavity of a patient, thereby repeating trials to impart a form; and then, the material is allowed to stand outside the oral cavity for polymerization or irradiated with light for polymerization, thereby completing the relining of the denture base.

The resin material for denture base that is used for such relining (rebasing) of a denture base has hitherto been constituted by a liquid made of methyl methacrylate as a major component and a powder made of polymethyl methacrylate or polyethyl methacrylate as a major component and having a polymerization catalyst added thereto. During the use, this resin material for denture base is required to be used under the conditions where necessary amounts of the liquid and the powder are weighed, uniformly mixed with each other, and allowed to stand for a certain period of time, whereby the mixture becomes into a dough-like state. However, according to this method, it is required that the powder and the liquid are weighed separately, and then mixed with each other, and hence, the operation is complicated; the mixed material in the dough-like state for a short time because the monomer has a high volatility; it is difficult to take a timing for building up on the mucosal surface of the denture base; and due to its odor or stimulation, an unpleasant feeling is imparted to an operator or a patient, and depending on circumstances, the health of the operator or patient is possibly injured.

In addition, with respect to the conventional art resin materials for denture base, though it is essential to mix the liquid and the powder with each other and to use the mixture, they involve such a defect that air is entrained during the mixing. The air entrained into the mixed material becomes air bubbles, leading to a reduction in physical properties such as strength and formation of minute irregularities on the denture base surface after curing, and causing staining or discoloration of the denture base or inducing an odor with a lapse of time. In recent years, in order to compensate these defects, a sheet-state photopolymerization type resin material for denture base that does not require mixing has been developed and provided. However, since the material before curing causes plastic deformation, this sheet-state photopolymerization type resin material for denture base involves such a defect that deformation is caused by pressure of a cheek mucosa, etc. or undercuts during the elimination from the oral cavity, thereby making it difficult to impress a precise state in the oral cavity to the material.

SUMMARY OF THE INVENTION

Thus, the present invention is aimed to provide a resin material for denture base that, even after mixing, is less in entrainment of air, is less in possibility to incorporate air bubbles into a mixed material, exhibits a proper elasticity during elimination from an oral cavity, not causing deformation, and can impress precisely the state in the oral cavity.

In order to achieve the above-described aim, we, the present inventors made extensive and intensive investigations. As a result, it has been found that by employing a two-pack mixing type liquid, the entrainment of air caused by mixing can be minimized and that it is useful to properly use monomers having a specific performance, leading to accomplishment of the invention.

In other words, it has been found the above-described aim can be achieved by a resin material for denture base comprising a combination of two liquids, in which one of the liquids is a solution of a polymer dissolved in a monomer having a high solubility to the polymer, and the other liquid is a solution of a polymer dispersed in a monomer that does not dissolve the polymer there in or having a low solubility to the polymer, leading to accomplishment of the present invention.

Specifically, the resin material for denture base according to the present invention is a two-pack type resin material for denture base constructed by the following components (a), (b) and (c):

(a) a methacrylate or acrylate monomer having at least one unsaturated double bond, (b) one or two or more polymers selected from the group consisting of a methacrylate polymer, an acrylate polymer, a methacrylate/acrylate copolymer, a methacrylate/styrene copolymer, and an acrylate/styrene copolymer, and (c) a polymerization initiator, wherein a liquid A comprises the polymer (b), the monomer (a) having a solubility to the polymer (b) of 20% by weight or more, and the polymerization initiator (c);

a liquid B comprises the polymer (b) and the monomer (a) having a solubility to the polymer (b) of less than 20% by weight; and when mixing the liquid A with the liquid B, the monomer (a) in the liquid A swells or dissolves the polymer (b) in the liquid B to increase its viscosity, whereby the mixture is polymerized and cured.

More specifically, the resin material for denture base according to the present invention is characterized in that two types of monomers having a different solubility to the polymer from each other are used and that a monomer having a high solubility to the polymer of 20% by weight or more is used in one of the liquids, while a monomer having a low solubility to the polymer of less than 20% by weight is used in the other liquid.

Concretely, the liquid A is one with a monomer having a high solubility to the polymer and having a viscosity adjusted by dissolving the polymer in the monomer. The liquid A has a performance such that when mixed with the liquid B later, its viscosity rapidly increases. Further, when the polymerization initiator is added to the liquid A, the liquid A will become polymerizable with an external energy such as a heat and light. On the other hand, the liquid B is one with a monomer that does not dissolve the polymer therein or has a low solubility to the polymer and has the like polymer as in the liquid A dispersed therein. As the polymer, are preferred polymers having a high solubility and a low glass transition point at normal temperature.

Such resin material for denture base comprising two liquids is extremely easy for mixing and is less in entrainment of air bubbles into a mixed material. In particular, when the resin material for denture base is filled in a cartridge where automatic mixing can be effected, the mixing can be carried out in a state free from air bubbles. When the polymer compounded in the liquid B is swollen by and dissolved in the monomer having a high solubility to the polymer to be compounded in the liquid A, the mixed material becomes into a dough-like state having a high viscosity and exhibits a proper elasticity. As a result, even when a few of undercuts or the like are present, the mixed material can impress precisely the shape in the oral cavity. Thereafter, the resulting mixed material is taken out from the oral cavity and irradiated with an external energy such as a heat and light to promote the polymerization of the monomer. Thus, it can function as a material for denture base.

DESCRIPTION OF THE PREFERRED EMBODIMENTS

The respective components of the resin material for denture base according to the present invention will be described below in detail.

Specific examples of the methacrylate or acrylate monomer having at least one unsaturated double bond as the component (a) include the following substances: methyl methacrylate, ethyl methacrylate, isopropyl methacrylate, 2-hydroxyethyl methacrylate, 3-hydroxypropyl methacrylate, 2-hydroxy-1,3-dimethacryloxypropane, n-butyl methacrylate, isobutyl methacrylate, butoxyethyl methacrylate, hydroxypropyl methacrylate, tetrahydrofurfuryl methacrylate, glycidyl methacrylate, 2-methoxyethyl methacrylate, 2-ethylhexyl methacrylate, benzyl methacrylate, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, polyoxytetramethylene glycol dimethacrylate, trimethylolethane trimethacrylate, pentaerythritol trimethacrylate, trimethylolmethane trimethacrylate, pentaerythritol tetramethacrylate, and acrylates corresponding to these methacrylates, 2,2-bis(methacryloxyphenyl)propane, 2,2-bis[4-(2-hydroxy-3-methacryloxypropoxy)phenyl]propane, 2,2-bis(4-methacryloxy-diethoxyphenyl)propane, and 2,2-bis(4-methacryloxy-polyethoxyphenyl)propane. Examples of the methacrylate or acrylate having a urethane bond in a molecule thereof include di-2-methacryloxyethyl-2,2,4-trimethylhexamethylene dicarbamate and a corresponding acrylate thereto. Besides, methacrylates or acrylates having a urethane bond and having a number of unsaturated double bonds can also be used. These methacrylates or acrylates can be used singly or in admixture. Preferably, a compounding amount of the methacrylate or acrylate monomer is 20 to 80% by weight to the liquid A and 50 to 90% by weight to the liquid B, respectively, and 20 to 90% by weight of the whole of the resin material for denture base.

It is necessary that the monomer used in the liquid A can dissolve therein at least 20% by weight of the polymer (b) as described later. In particular, are suitably used monomers having a solubility of 50% by weight or more to the polymer (b) such as 1, 6-hexanediol dimethacrylate, ethylene glycol dimethacrylate, trimethylolpropane trimethacrylate, and butoxyethyl methacrylate. On the other hand, it is necessary that the monomer used in the liquid B has a solubility of less than 20% by weight to the polymer (b) as described later. In particular, are suitably used monomers that do not substantially dissolve the polymer (b) such as polyoxytetramethylene glycol dimethacrylate therein.

Specific examples of one or two or more polymers selected from the group consisting of a methacrylate polymer, an acrylate polymer, a methacrylate/acrylate copolymer, a methacrylate/styrene copolymer, and an acrylate/styrene copolymer as the component (b) include the following polymers: homopolymers or copolymers of methyl methacrylate, ethyl methacrylate, butyl methacrylate, isobutyl methacrylate, tertiary butyl methacrylate, ethylhexyl methacrylate, lauryl methacrylate, dodecyl methacrylate, stearyl methacrylate, cyclohexyl methacrylate, benzyl methacrylate, isobonyl methacrylate, glycidyl methacrylate, hydroxyethyl methacrylate, hydroxypropyl methacrylate, methoxyethyl methacrylate, and ethoxyethyl methacrylate, or of corresponding acrylates thereto; and copolymers of these methacrylates or acrylates and styrene. In these polymers for the component (b), are preferred polymers as prepared by using azobisisobutyronitrile as a polymerization initiator during the preparation of the polymer.

Of these polymers for the component (b), is preferred at least one polymer having a solubility of 20% by weight or more to the monomer (a) of the liquid A, which is selected from homopolymers of methyl methacrylate, ethyl methacrylate, butyl methacrylate, and isobutyl methacrylate, or of corresponding acrylates thereto; a methyl methacrylate/ethyl methacrylate copolymer; a methyl methacrylate/ethyl acrylate copolymer; a methyl acrylate/ethyl methacrylate copolymer; a methyl acrylate/ethyl acrylate copolymer; a methyl methacrylate/butyl methacrylate copolymer; a methyl methacrylate/butyl acrylate copolymer; a methyl acrylate/butyl methacrylate copolymer; a methyl acrylate/butyl acrylate copolymer; a methyl methacrylate/isobutyl methacrylate copolymer; amethylmethacrylate/isobutyl acrylate copolymer; a methyl acrylate/isobutyl methacrylate copolymer; a methyl acrylate/isobutyl acrylate copolymer; and a methyl methacrylate/styrene copolymer. Preferably, a compounding amount of the polymer (b) is 20 to 80% by weight to the liquid A and 10 to 50% by weight to the liquid B, respectively, and 5 to 80% by weight of the whole of the resin material for denture base.

The polymerization initiator as the component (c) is appropriately selected depending on the polymerization mode to be used and then added. As a heat polymerization type, are mainly used organic peroxides, azo compounds, and the like. As the organic peroxides, are preferred diacyl peroxides having an aromatic ring and peroxy esters considered to be esters of perbenzoic acid. Effective examples include benzoyl peroxide, 2,4-dichlorobenzoyl peroxide, m-tolyl peroxide, t-butyl peroxybenzoate, di-t-butyl peroxyisophthalate, 2,5-dimethyl-2,5-di(benzoyl peroxy) hexane, and 2,5-dimethyl-2,5-di{(o-benzoyl)benzoyl peroxy}hexane. As the azo compounds, is useful azobisisobutyronitrile. In addition, organometallic compounds such as tributylboron can be used. A suitable compounding amount of the component (c) is 0.01 to 5 parts by weight based on 100 parts by weight of the liquid A.

As a low temperature polymerization type, are enumerated combinations of an organic peroxide with an aromatic tertiary amine. In this case, one of the liquids is compounded with the organic peroxide, while the other liquid is compounded with the aromatic tertiary amine. As the organic peroxide, are useful the same organic peroxides used for the heat polymerization type as described above.

As the tertiary amine, are preferred aromatic tertiary amines in which a nitrogen atom is substituted directly on the aromatic group. Effective examples include N,N-dimethyl-p-toluidine, N,N-dimethylaniline, N-methyl-N-β-hydroxyaniline, N,N-di(β-hydroxyethyl)-aniline, N,N-di(β-hydroxyethyl)-p-toluidine, N,N-di(β-hydroxypropyl)-aniline, N,N-di(β-hydroxypropyl)-p-toluidine, ethylN,N-dimethylaminobenzoate, and isoamyl N,N-dimethylaminobenzoate.

A suitable amount of the low temperature polymerization type polymerization initiator to be added is 0.01 to 5 parts by weight for each of the organic peroxide and the aromatic tertiary amine based on 100 parts by weight of each of the liquids.

Further, it is also possible to impart a photopolymerization function to the polymerization initiator. In this case, a combination of a sensitizer with a reducing agent is generally employed as the photopolymerization initiator. Examples of the sensitizer include camphorquinone, benzil, diacetyl, benzyl dimethyl ketal, benzyl diethyl ketal, benzyl di(2-methoxyethyl) ketal, 4,4'-dimethybenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethyl-thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl) ketone, 4,4'-bisdiethylamino-benzophenone, and acyl phosphine oxide derivatives, and azide group-containing compounds. These sensitizers can be used singly or in admixture.

As the reducing agent, are generally employed tertiary amines. As the tertiary amines, are preferred N,N-dimethyl-p-toluidine, N,N-dimethylaminoethyl methacrylate, triethanolamine, methyl 4-dimethylaminobenzoate, ethyl 4-dimethylaminobenzoate, and isoamyl 4-dimethylaminobenzoate. As other reducing agents, are enumerated benzoyl peroxide, sodium sulfinate derivatives, organometallic compounds, and the like.

A suitable amount of the photopolymerization type polymerization initiator to be added is 0.01 to 5 parts by weight based on 100 parts by weight of the liquid A.

In the case of the photopolymerization type resin material for denture base, the polymerization reaction is achieved upon irradiation with actinic rays such as ultraviolet rays and visible rays. As a light source, are employable various super-high, high, medium and low pressure mercury vapor lamps, chemical lamps, carbon arc lamps, metal halide lamps, fluorescent lamps, tungsten lamps, xenon lamps, and argon ion lasers.

If desired, a filler is added as a component (d) to the resin material for denture base according to the present invention, whereby the stability of the liquid can be improved, or the strength of a cured material can be enhanced. As the filler as the component (d), are usually used inorganic fillers. Specific examples include glasses such as silicon dioxide, barium glass, alumina glass, and potassium glass; and powders such as synthetic zeolite, calcium phosphate, feldspar, aluminum silicate, calcium silicate, magnesium carbonate, and quartz. These inorganic fillers may be subjected to a surface processing with γ-methacryloxypropyl trimethoxysilane, vinyl trichlorosilane, vinyl triethoxysilane, vinyl trimethoxysilane, vinyl triacetoxysilane, vinyl tri(methoxyethoxy)silane, etc. Also, so-called organic-inorganic composite fillers prepared by previously mixing the above-described inorganic filler with the polymerizable monomer and curing the mixture, followed by crashing, and crosslinked polymer powders that are insoluble in the polymerizable monomer can be used. A suitable amount of such filler to be compounded is 1 to 50 parts by weight based on 100 part by weight of the liquid A and/or 100 parts by weight of the liquid B. When the amount of the filler is less than 1 part by weight, no effect by the addition is observed. On the other hand, when it exceeds 50 parts by weight, the paste becomes hard, whereby the operability is lowered.

In addition, if desired, trace amounts of known ultraviolet light absorbers, coloring agents, polymerization inhibitors, discoloration preventives, fungicides, plasticizers, surfactants, etc. can be used.

In the resin material for denture base according to the present invention, the liquid A and the liquid B are mixed with each other, and the mixed material is provided for use. The resin material for denture base according to the present invention is markedly improved in the mixing operability as compared with those of the conventional art in which a powder and a liquid are mixed with each other. And, the resin material for denture base according to the present invention is filled in a cartridge where automatic mixing can be effected and then provided for the use. Thus, it is possible to make the material automatically mixed in the cartridge have a viscosity such that it can be inserted directly into an oral cavity without need of weighing and mixing, whereby the operability is further improved. Further, a viscosity of the resin material for denture base according to the present invention increases in the oral cavity so that it becomes into a dough-like state having a proper elasticity. Thus, the resulting material does not cause deformation during the elimination from the oral cavity, so that it can precisely impress the state in the oral cavity.

Next, the present invention will be described below in detail with reference to the following Examples, but it should not be construed that the present invention is limited thereto.

EXAMPLE 1

| (Liquid A) | |
|---|---|
| 1,6-Hexanediol dimethacrylate | 60% by weight |
| Butoxyethyl methacrylate | 20% by weight |
| Methyl methacrylate/ethyl methacrylate copolymer | 20% by weight |
| Benzoyl peroxide (0.15 parts by weight based on 100 parts by weight of the total sum of the above-described three components) | |
| (Liquid B) | |
| Polyoxytetramethylene glycol dimethacrylate | 70% by weight |
| Methyl methacrylate/ethyl methacrylate copolymer | 30% by weight |

The respective components were weighed and thoroughly mixed to prepare a resin material for denture base comprising the liquid A and liquid B. Incidentally, in the liquid A, all of the methyl methacrylate/ethyl methacrylate copolymer was dissolved in 1,6-hexanediol dimethacrylate, and in the liquid B, the methyl methacrylate/ethyl methacrylate copolymer was not substantially dissolved in polyoxytetramethylene glycol dimethacrylate.

Equal amounts of the liquid A and the liquid B of the thus obtained resin material for denture base were collected and measured for bending strength, elastic strain, and elastic energy in the manners as described later. As a result, the bending strength, the elastic strain, and the elastic energy were 40 MPa, 30%, and 3.05 MPa, respectively.

Also, this mixed resin material for denture base was filled in a cavity formed in an investment in a flask, heated in warm water at 70° C. for 90 minutes, and then heated for polymerization in hot water at 100° C. for 30 minutes, to prepare a rebase for denture base. This resin material for denture base was extremely easy for mixing and was free from incorporation of air bubbles and from odor or stimulation. Even when the completed denture was set for one month, were not observed discoloration, staining, and the like caused by the generation of air bubbles.

Measurement of bending strength, elastic strain and elastic energy

In the case where a thermal polymerization catalyst was used, the whole of the flask was heated in warm water at 70° C. for 90 minutes and then in hot water at 100° C. for 30 minutes, thereby effecting polymerization and curing. In the case where a photopolymerization catalyst was used, the resin material for denture base was filled in a metallic mold and irradiated with visible light beams for 5 minutes by means of a dental visible light irradiator (a trade name: LABOLIGHT LV-II, manufactured by GC Corporation), thereby effecting polymerization and curing. Thus, there was prepared a specimen in a rectangular parallelopiped state having a size of 2 mm×2 mm×25 mm.

This specimen was immersed in distilled water at 37° C. for 24 hours and then subjected to a three-point bending test at a span of 20 mm and at a cross head speed of 1 mm/min. by means of a universal testing machine (a trade name: Autograph, manufactured by Shimadzu Corporation), thereby measuring a bending strength, an elastic strain, and an elastic energy.

EXAMPLE 2

| (Liquid A) | |
|---|---|
| 1,6-Hexanediol dimethacrylate | 60% by weight |
| Butoxyethyl methacrylate | 20% by weight |
| Methyl methacrylate/ethyl methacrylate copolymer | 20% by weight |
| Camphorquinone (0.5 parts by weight based on 100 parts by weight of the total sum of the above-described three components) | |
| Ethyl 4-dimethylaminobenzoate (1.5 parts by weight based on 100 parts by weight of the total sum of the above-described three components) | |
| (Liquid B) | |
| Polyoxytetramethylene glycol dimethacrylate | 70% by weight |
| Methyl methacrylate/ethyl methacrylate copolymer | 30% by weight |

The respective components were weighed and thoroughly mixed to prepare a resin material for denture base comprising the liquid A and liquid B. Incidentally, in the liquid A, all of the methyl methacrylate/ethyl methacrylate copolymer was dissolved in 1, 6-hexanediol dimethacrylate, and in the liquid B, the methyl methacrylate/ethyl methacrylate copolymer was not substantially dissolved in polyoxytetramethylene glycol dimethacrylate.

The thus obtained resin material for denture base was measured for bending strength, elastic strain and elastic energy in the same manner as in Example 1. As a result, the bending strength, the elastic strain, and the elastic energy were 38 MPa, 30%, and 2.95 MPa, respectively.

Further, after applying an adhesive (a trade name: Denture Primer, made by GC Corporation) onto a denture base in which one layer on a mucosal surface had been deleted, equal amounts of the liquid A and the liquid B were mixed with each other, and the mixed material was built up on the denture base. The resulting denture base was inserted into an oral cavity and subjected to impression taking for the form of the mucosal surface, followed by elimination from the oral cavity. After applying an air barrier material (a trade name: MILD REBARON Air Barrier Material, made by GC Corporation), the resulting denture base was irradiated with visible light beams for 5 minutes by means of a dental visible light curing unit (a trade name: LABOLIGHT LV-II, manufactured by GC Corporation), thereby effecting polymerization and curing. Thus, the relining of the denture base was completed. In this relining operation, a series of the operations for weighing and mixing were very simple, as compared with the case of the resin materials for denture base of the conventional art requiring mixing the liquid and the powder. In addition, the denture base was free from incorporation of air bubbles. Moreover, during insertion into the oral cavity, no monomer odor was presented, and during making trials in the oral cavity, no stimulation occurred. Even when the relining-completed denture base was set for one month, neither discoloration nor staining was observed.

EXAMPLE 3

| (Liquid A) | |
|---|---|
| Trimethylolpropane trimethacrylate | 80% by weight |
| Methyl methacrylate/ethyl methacrylate copolymer | 20% by weight |
| Camphorquinone (0.5 parts by weight based on 100 parts by weight of the total sum of the above-described two components) | |
| Ethyl 4-dimethylaminobenzoate (0.5 parts by weight based on 100 parts by weight of the total sum of the above-described two components) | |
| (Liquid B) | |
| Polyoxytetramethylene glycol dimethacrylate | 70% by weight |
| Methyl methacrylate/ethyl methacrylate copolymer | 30% by weight |

The respective components were weighed and thoroughly mixed to prepare a resin material for denture base comprising the liquid A and liquid B. Incidentally, in the liquid A, all of the methyl methacrylate/ethyl methacrylate copolymer was dissolved in trimethylolpropane trimethacrylate, and in the liquid B, the methylmethacrylate/ethyl methacrylate copolymer was not substantially dissolved in polyoxytetramethylene glycol dimethacrylate.

The thus obtained resin material for denture base was measured for bending strength, elastic strain and elastic energy in the same manner as in Example 1. As a result, the bending strength, the elastic strain, and the elastic energy were 41 MPa, 25%, and 2.80 MPa, respectively.

Further, the relining of the denture base was carried out in the same manner as in Example 2. As a result, the denture base was free from incorporation of air bubbles. Moreover, during insertion into the oral cavity, no monomer odor was presented, and during making trials in the oral cavity, no stimulation occurred. Even when the relining-completed denture base was set for one month, neither discoloration nor staining was observed.

EXAMPLE 4

| (Liquid A) | |
|---|---|
| Ethylene glycol dimethacrylate | 80% by weight |
| Methyl methacrylate/ethyl methacrylate copolymer | 20% by weight |
| Camphorquinone (0.5 parts by weight based on 100 parts by weight of the total sum of the above-described two components) | |
| Ethyl 4-dimethylaminobenzoate (1.5 parts by weight based on 100 parts by weight of the total sum of the above-described two components) | |
| (Liquid B) | |
| Polyoxytetramethylene glycol dimethacrylate | 70% by weight |
| Methyl methacrylate/ethyl methacrylate copolymer | 30% by weight |

The respective components were weighed and thoroughly mixed to prepare a resin material for denture base comprising the liquid A and liquid B. Incidentally, in the liquid A, all of the methyl methacrylate/ethyl methacrylate copolymer was dissolved in ethylene glycol dimethacrylate, and in the liquid B, the methyl methacrylate/ethyl methacrylate copolymer was not substantially dissolved in polyoxytetramethylene glycol dimethacrylate.

The thus obtained resin material for denture base was measured for bending strength, elastic strain and elastic energy in the same manner as in Example 1. As a result, the bending strength, the elastic strain, and the elastic energy were 40 MPa, 25%, and 2.70 MPa, respectively.

Further, the relining of the denture base was carried out in the same manner as in Example 2. As a result, the denture base was free from incorporation of air bubbles. Moreover, during insertion into the oral cavity, no monomer odor was presented, and during making trials in the oral cavity, no stimulation occurred. Even when the relining-completed denture base was set for one month, neither discoloration nor staining was observed.

EXAMPLE 5

| (Liquid A) | |
|---|---|
| 1,6-Hexanediol dimethacrylate | 60% by weight |
| Butoxyethyl methacrylate | 20% by weight |
| Ethyl methacrylate polymer | 20% by weight |
| Camphorquinone (0.5 parts by weight based on 100 parts by weight of the total sum of the above-described three components) | |
| Ethyl 4-dimethylaminobenzoate (1.5 parts by weight based on 100 parts by weight of the total sum of the above-described three components) | |
| (Liquid B) | |
| Polyoxytetramethylene glycol dimethacrylate | 70% by weight |
| Methyl methacrylate/ethyl methacrylate copolymer | 30% by weight |

The respective components were weighed and thoroughly mixed to prepare a resin material for denture base comprising the liquid A and liquid B. Incidentally, in the liquid A, all of the ethyl methacrylate polymer was dissolved in 1,6-hexanediol dimethacrylate and butoxyethyl methacrylate, and in the liquid B, the methyl methacrylate/ethyl methacrylate copolymer was not substantially dissolved in polyoxytetramethylene glycol dimethacrylate.

The thus obtained resin material for denture base was measured for bending strength, elastic strain and elastic energy in the same manner as in Example 1. As a result, the bending strength, the elastic strain, and the elastic energy were 35 MPa, 35%, and 3.25 MPa, respectively.

Further, the relining of the denture base was carried out in the same manner as in Example 2. As a result, the denture base was free from incorporation of air bubbles. Moreover, during insertion into the oral cavity, no monomer odor was presented, and during making trials in the oral cavity, no stimulation occurred. Even when the relining-completed denture base was set for one month, neither discoloration nor staining was observed.

EXAMPLE 6

| (Liquid A) | |
|---|---|
| 1,6-Hexanediol dimethacrylate | 60% by weight |
| Butoxyethyl methacrylate | 20% by weight |
| Ethyl methacrylate polymer | 20% by weight |
| Camphorquinone | |
| (0.5 parts by weight based on 100 parts by weight of the total sum of the above-described three components) | |
| Ethyl 4-dimethylaminobenzoate | |
| (1.5 parts by weight based on 100 parts by weight of the total sum of the above-described three components | |
| (Liquid B) | |
| Polyoxytetramethylene glycol dimethacrylate | 60% by weight |
| Methyl methacrylate polymer | 30% by weight |
| Colloidal silica | 10% by weight |

The respective components were weighed and thoroughly mixed to prepare a resin material for denture base comprising the liquid A and liquid B. Incidentally, in the liquid A, all of the ethyl methacrylate polymer was dissolved in 1, 6-hexanediol dimethacrylate and butoxyethyl methacrylate, and in the liquid B, the methyl methacrylate polymer was not substantially dissolved in polyoxytetramethylene glycol dimethacrylate.

The thus obtained resin material for denture base was measured for bending strength, elastic strain and elastic energy in the same manner as in Example 1. As a result, the bending strength, the elastic strain, and the elastic energy were 45 MPa, 28%, and 3.50 MPa, respectively.

Further, the relining of the denture base was carried out in the same manner as in Example 2. As a result, the denture base was free from incorporation of air bubbles. Moreover, during insertion into the oral cavity, no monomer odor was presented, and during making trials in the oral cavity, no stimulation occurred. Even when the relining-completed denture base was set for one month, neither discoloration nor staining was observed.

COMPARATIVE EXAMPLE 1

As the conventional art powder-liquid type resin material for denture base, was used a relining material for denture base (a trade name: GC REBARON LC, made by GC Corporation). According to the instructions in the specification, the liquid and the powder were weighed, and mixed with each other. The mixed material was measured for bending strength, elastic strain and elastic energy in the same manner as in Example 1. Rs a result, the bending strength, the elastic strain, and the elastic energy were 65 MPa, 5%, and 0.88 MPa, respectively.

Further, the relining of the denture base was carried out in the same manner as in Example 2. As a result, the operations including weighing and mixing were complicated, and an unpleasant monomer odor was presented during the operations. When the completed denture base was set for one month, minute irregularities due to air bubbles generated were observed on the surface, and staining was observed in that site.

As described above in detail, the resin material for denture base according to the present invention is a two-pack mixing type resin material for denture base comprising a novel combination of a monomer and a polymer, which has not been achieved hitherto. The resin material for denture base according to the present invention is extremely easy for mixing operations and is less in incorporation of air bubbles into the mixed material. Thus, it is superior in physical nature and esthetics, and can achieve relining of a denture base that is free from staining and an odor, etc. even when used for a long period of time. Accordingly, the resin material for denture base according to the present invention is greatly valuable in contributing to the dental remedy.

While the present invention has been described in detail and with reference to specific embodiments thereof, it will be apparent to one skilled in the art that various changes and modifications can be made therein without departing from the spirit and scope thereof.

What is claimed is:

1. A resin material for denture base having two liquids comprising a liquid A and a liquid B, comprising the following components (a), (b) and (c):
   (a) a methacrylate or acrylate monomer having at least one unsaturated double bond,
   (b) one or more polymers selected from the group consisting of a methacrylate polymer, an acrylate polymer, a methacrylate/acrylate copolymer, a methacrylate/styrene copolymer, and an acrylate/styrene copolymer, and
   (c) a polymerization initiator,
   wherein the liquid A comprises the polymer (b), the monomer (a) wherein said monomer (a) has a solubility to the polymer (b) of 20% by weight or more, and the polymerization initiator (c); and
   wherein the liquid B comprises the polymer (b) and the monomer (a) wherein said monomer (a) has a solubility to the polymer (b) of less than 20% by weight; and
   when mixing the liquid A with the liquid B, the monomer (a) in the liquid A swells or dissolves the polymer (b) in the liquid B to increase its viscosity, whereby the mixture is polymerized and cured.

2. The resin material for denture base as claimed in claim 1, wherein the monomer (a) in the liquid A is one or more polymerizable monomers and/or oligomers selected from the group consisting of ethylene glycol dimethacrylate, trimethylolpropane trimethacrylate, 1,6-hexanediol dimethacrylate, butoxyethyl methacrylate, benzyl methacrylate, and polyoxytetramethylene glycol dimethacrylate.

3. The resin material for denture base as claimed in claim 1, wherein in the liquid B, the monomer (a) ispolyoxytetramethyleneglycol dimethacrylate, and the polymer (b) is an ethyl methacrylate polymer, a methyl methacrylate/ethyl methacrylate copolymer, or an ethyl methacrylate polymer and a methyl methacrylate/ethyl methacrylate copolymer.

4. The resin material for denture base as claimed in claim 1, wherein the polymerization initiator (c) is a heat polymerization type.

5. The resin material for denture base as claimed in claim 1, wherein the polymerization initiator (c) is a low temperature polymerization type.

6. The resin material for denture base as claimed in claim 1, wherein the polymerization initiator (c) is a combination of a photopolymerization initiator with a reducing agent.

7. The resin material for denture base as claimed in claim 1, further comprising a filler (d) that is insoluble in the monomer (a), wherein said filler (d) is in an amount of 1 to 50 parts by weight based on 100 parts by weight of the liquid A and/or 100 parts by weight of the liquid B.

8. The resin material for denture base as claimed in claim 1, wherein liquid A comprises 20 to 80% by weight of monomer (a).

9. The resin material for denture base as claimed in claim 1, wherein liquid B comprises 50 to 90% by weight of monomer (a).

10. The resin material for denture base as claimed in claim 1, wherein the resin material for denture b comprises 20 to 90% by weight of monomer (a).

11. The resin material for denture base as claimed in claim 1, wherein liquid A comprises 20 to 80% by weight of monomer (b).

12. The resin material for denture base as claimed in claim 1, wherein liquid B comprises 10 to 50% by weight of monomer (b).

13. The resin material for denture base as claimed in claim 1, wherein the resin material for denture b comprises 5 to 80% by weight of monomer (b).

14. The resin material for denture base as claimed in claim 4, wherein the polymerization initiator (c) is an organic peroxide or an azo compound.

15. The resin material for denture base as claimed in claim 4, wherein liquid A comprises 0.01 to 5 parts by weight of the polymerization initiator (c), based on 100 parts by weight of liquid A.

16. The resin material for denture base as claimed in claim 5, wherein the polymerization initiator (c) is an organic peroxide with an aromatic tertiary amine.

17. The resin material for denture base as claimed in claim 5, wherein liquid A comprises 0.01 to 5 parts by weight of the polymerization initiator (c), based on 100 parts by weight of liquid A.

18. The resin material for denture base as claimed in claim 6, wherein liquid A comprises 0.01 to 5 parts by weight of the polymerization initiator (c), based on 100 parts by weight of liquid A.

* * * * *